(12) United States Patent
Barker et al.

(10) Patent No.: US 11,639,867 B2
(45) Date of Patent: May 2, 2023

(54) APPARATUS FOR MEASURING LEVELS OF MATERIALS

(71) Applicant: JOHNSON MATTHEY PUBLIC LIMITED COMPANY, London (GB)

(72) Inventors: Graham Barker, Billingham (GB); Carl Robert Tipton, Billingham (GB); Daniel James Whiting, Billingham (GB)

(73) Assignee: Johnson Matthey Public Limited Company, London (GB)

( * ) Notice: Subject to any disclaimer, the term of this patent is extended or adjusted under 35 U.S.C. 154(b) by 180 days.

(21) Appl. No.: 17/310,182

(22) PCT Filed: Jan. 14, 2020

(86) PCT No.: PCT/GB2020/050064
§ 371 (c)(1),
(2) Date: Jul. 23, 2021

(87) PCT Pub. No.: WO2020/178544
PCT Pub. Date: Sep. 10, 2020

(65) Prior Publication Data
US 2022/0082425 A1 Mar. 17, 2022

(30) Foreign Application Priority Data
Mar. 7, 2019 (GB) .................................... 1903101

(51) Int. Cl.
*G01F 23/284* (2006.01)
*G01N 33/28* (2006.01)

(52) U.S. Cl.
CPC ....... *G01F 23/284* (2013.01); *G01N 33/2823* (2013.01)

(58) Field of Classification Search
CPC .......................... G01F 23/284; G01N 33/2823
See application file for complete search history.

(56) References Cited

U.S. PATENT DOCUMENTS

| 4,107,993 | A | 8/1978 | Shuff et al. |
| 6,782,736 | B1 | 8/2004 | Hammer |

(Continued)

FOREIGN PATENT DOCUMENTS

| CN | 201421346 Y | 3/2010 |
| CN | 102052952 A | 5/2011 |

(Continued)

*Primary Examiner* — David Z Huang
*Assistant Examiner* — Jean F Morello
(74) *Attorney, Agent, or Firm* — BakerHostetler

(57) ABSTRACT

An apparatus for determining the identity, location, or level of one or more material phases or the location of an interface between two material phases within a defined volume having, a linear array of units configured to generate and detect electromagnetic radiation; an elongate enclosure containing the array of units, being at least partially transparent to the electromagnetic radiation generated by the units; the apparatus being configured to be at least partially submerged within the one or more material phases within the defined volume, the linear array of units being configured to generate transmission signals through the at least partially transparent elongate enclosure to the one or more material phases surrounding the enclosure at locations along the length of the enclosure, and to receive return signals through the elongate enclosure at locations along the length of the enclosure from the one or more material phases surrounding the enclosure.

15 Claims, 7 Drawing Sheets

(56) References Cited

U.S. PATENT DOCUMENTS

| | | | |
|---|---|---|---|
| 9,464,888 B2* | 10/2016 | Huang | G01B 15/00 |
| 2003/0117150 A1 | 6/2003 | Constant | |
| 2004/0229376 A1 | 11/2004 | Beauducel | |
| 2015/0177163 A1 | 6/2015 | Edvardsson | |
| 2016/0008742 A1 | 1/2016 | Adler et al. | |
| 2016/0202105 A1 | 7/2016 | Baer et al. | |
| 2016/0265959 A1 | 9/2016 | Blodt et al. | |
| 2018/0058901 A1 | 3/2018 | Moermann et al. | |

FOREIGN PATENT DOCUMENTS

| | | |
|---|---|---|
| CN | 109781211 A | 5/2019 |
| DE | 10133692 A1 | 2/2002 |
| EP | 1126251 A2 | 8/2001 |
| EP | 1235059 A1 | 8/2002 |
| EP | 1382946 A1 | 1/2004 |
| FR | 2791131 A1 | 9/2000 |
| GB | 2501165 A | 10/2013 |
| WO | 00/22387 A1 | 4/2000 |
| WO | 03/012379 A1 | 2/2003 |
| WO | 2006/084263 A2 | 8/2006 |
| WO | 2008/052274 A1 | 5/2008 |

* cited by examiner

APPARATUS FOR MEASURING LEVELS OF MATERIALS

FIELD OF INVENTION

The present invention relates to methods of measuring the level of materials as well as apparatus for measuring levels of materials, especially of fluids. The present invention has particular, but not exclusive, application to the measurement of levels of fluid in separators, particularly oil/water separators, especially to the location of gas-oil and oil-water boundaries in separation vessels in oil production installations.

BACKGROUND

It is often necessary to separate aqueous, oil and gas phases that form the flow from a production well. Water and gas are naturally co-produced with oil and water may even be injected into oilfields to maintain the production of oil. This results in a stream from the production well comprising a mixture of oil, gas, and water. Minerals, such as sand, and heavy oil or tar material may also be present. It is therefore necessary to separate these components from one another before further processing.

Typically, such separation is carried out in a separation system which may include a pre-separation means, such as a cyclone, to separate much of any gaseous phase present from the liquid phases and usually also includes a separation vessel in which the fluid flow is slowed and allowed to separate into layers which are then separately taken off from the separation vessel. The means for removing the respective phases are usually fixed within the separation vessel and so it is necessary to control the rate at which the mixture of oil and water and any other components is provided to the vessel and to also control the rate at which the separated components are removed from the vessel. Controlling the rates of inflow and outflow controls the levels of the separated components within the vessel and the levels of the components are maintained to enable their ready removal from the separator. In practice, the separation of phases is made more difficult by foam formed by liquid and gas phases, and dispersions or emulsions of aqueous and oil phases. The presence of foams or emulsions makes the inter-phase boundaries less definite and thereby makes overall control more difficult. The operation of such separators is complicated because it is difficult to determine the location of phase boundaries.

Level and density measurement systems, for example for use in measuring the level and/or density of a material within a vessel or other defined volume, are known. It is also known to locate the boundaries between different materials in a vessel by measuring the density of the vessel contents at different locations to form a density profile of the vessel and contents in order to identify density changes which are indicative of boundary regions. For example, it has been proposed in WO 00/22387 to measure the density profile of a medium by providing an array of radioactive sources of gamma radiation to give collimated beams of said radiation and an array of detectors disposed so that the medium under study extends between the sources and the detectors. By monitoring the radiation received by the detectors, the amount of radiation absorbed by the medium from each beam can be determined and so variations in the medium density can be detected.

A method and apparatus for level measurement using microwaves is described in U.S. Pat. No. 4,107,993. The apparatus comprises using the absorption of microwave energy to indicate small changes in the level of a liquid in a vessel in order to control the level of the liquid. The apparatus comprises an external chamber similar to a sight gauge and an external microwave source and an external microwave receiver. Unabsorbed microwave energy passing through the external chamber is measured and the level of the liquid is inferred. EP1126251 describes a similar apparatus in which an external tank is used, although in this apparatus, the microwave generator is located such that the microwaves are directed down towards the surface of the liquid and relies on reflection from the surface rather than passing through the liquid and relying on transmission to determine the level of the liquid. EP1235059 also describes a microwave level measurement apparatus in which a microwave generator is configured to measure the level of the liquid based on reflection.

US2004/0229376 discloses a method for determining the composition of a homogeneous fluid, for example a petroleum effluent on flow, an emulsion consisting of water and oil, or a foam consisting of oil and gas. The attenuation and the phase shift of microwave beams that have traversed a fluid of unknown composition with paths of different lengths between emitters and detectors are measured.

US2003/0117150 discloses a separating drum which is provided with a device for determining the position, the composition and the nature of several layers of fluid. The device comprises a first rod provided with microwave beam emitters, a second rod provided with microwave beam receivers, a microwave source that can be connected to the emitters, and means for recording and analysing the microwave beams received by receivers.

Both US2004/0229376 and US2003/0117150 comprise a linear array of transmitters and a separate linear array of detectors which are spaced apart from the transmitters. Both the array of transmitters and the array of detectors are disposed in a fluid column such that the fluid fills the space between the transmitters and the detectors and microwave beams pass through the fluid from the transmitters to the detectors. This configuration is bulky and requires alignment of transmitters and detectors. Furthermore, microwaves can be severely attenuated in certain types of fluid affecting performance or requiring high power microwave transmitters. In the alternative, certain types of fluid are substantially transparent to microwave radiation and thus an accurate measurement based on absorption of microwave radiation transmitted through the fluid is not possible.

US2015/0177163 discloses a system and method for determining a density of a non-conducting medium in a tank where the relationship between a dielectric constant and a density of the medium is known. The system comprises a transceiver, and a waveguide, the waveguide extends towards and into the medium. The system further comprises a first microwave resonator located on a support structure alongside the waveguide. The first microwave resonator has a resonance frequency, which depends on a dielectric constant of a medium surrounding the resonator according to a known relationship, and is arranged to reflect a portion in the frequency domain of a signal being guided along the waveguide. This is a variant of a Time-Domain Reflectometry (TDR) system. This type of prior art configuration uses a transmission line which does not isolate the transmission signal from the surrounding media. The signal interacts with the media down the transmission line and is reflected at interfaces of the surrounding media. The problem with this approach is that the transmission signal cannot penetrate certain interfaces. DE10133692 also discloses a similar Time-Domain Reflectometry (TDR) system.

It is an object of the present invention to provide an improved measurement system, apparatus and method for the measurement of a level or location or identity of a material, and to overcome the limitations of the prior art.

SUMMARY OF THE INVENTION

The present specification provides an apparatus for determining the identity, location or level of one or more material phases or the location of an interface between two material phases within a defined volume, the apparatus comprising:
   a) a linear array of units configured to generate and detect electromagnetic radiation (e.g. microwaves);
   b) an elongate enclosure containing the array of units, the elongate enclosure being at least partially transparent to the electromagnetic radiation generated by the units;
   the apparatus being configured to be at least partially submerged within the one or more material phases within the defined volume with the linear array of units being physically isolated from the one or more materials by the elongate enclosure,
   the linear array of units being configured to generate transmission signals through the at least partially transparent elongate enclosure to the one or more material phases surrounding the enclosure at locations along the length of the enclosure, and to receive return signals through the elongate enclosure at locations along the length of the enclosure from the one or more material phases surrounding the enclosure,
   wherein the apparatus is configured to process the return signals to determining the identity, location or level of the one or more material phases or the location of an interface between two material phases within the defined volume.

The apparatus differs from configurations such as those described in US2004/0229376 and US2003/0117150 in that rather than providing spaced apart arrays of transmitters and detectors and measuring absorption of electromagnetic radiation as it passes through a material located between the emitters and detectors, the present configuration provides a single array of units for emitting and detecting electromagnetic radiation, with the array of units being isolated from the surrounding medium by an enclosure which is at least partially transparent to the electromagnetic radiation. The units can thus transmit electromagnetic radiation though the enclosure at locations along the enclosure and measure a return signal which is dependent on the material surrounding the enclosure at each of the locations along the enclosure. This configuration is compact and is not reliant on absorption of electromagnetic radiation. The configuration can be used to accurately measure the location of a wide range of materials in a vessel.

Furthermore, the apparatus differs from Time-Domain Reflectometry (TDR) systems, such as described in US2015/0177163, in that the transmission lines of prior art TRD systems are not isolated from the surrounding media such that a signal passing down the line will reflect from an interface. As previously describes, the problem with this approach is that the transmission signal cannot penetrate certain interfaces. In contrast, the apparatus as described herein comprises an array of units for emitting and detecting electromagnetic radiation which are isolated from the surrounding material and transmit and detect at different depths. As such, the apparatus of the present invention does not have the same problem of penetrating interfaces from above and can reliably detect all layers of materials regardless of the type and number of interfaces present in a material column.

The enclosure, which may be a dip pipe, can be at least partially comprised of ceramic, plastic, or metal and may comprise one or more windows which are more transparent to electromagnetic radiation than the rest of the enclosure, the units being configured to transmit and receive electromagnetic radiation through the windows.

The apparatus may further comprise one or more support members which retain the units within the enclosure at locations along the enclosure, the one or more support members configured to position and orientate the units to transmit and receive electromagnetic radiation through the enclosure at locations along the enclosure. The apparatus may also be modular such that units can be detachably coupled to the linear array of units to extend the length of the linear array of units.

The present specification also provides a method for determining a location, identity or level of one or more material phases or the location of an interface between two material phases within a defined volume, said method comprising:
   a) positioning the apparatus as previously described within the material in the defined volume;
   b) causing the array of units to generate electromagnetic radiation;
   c) measuring the returned electromagnetic radiation using the array of units; and
   d) determining the location, identity or level of one or more materials or the location of an interface between two materials within the defined volume based on the measurement of the returned electromagnetic radiation.

Also described herein is a method for measuring a location, identity, or level of one or more material phases or the location of an interface between two material phases within a defined volume, said method comprising:
   a) providing one or more units configured to generate electromagnetic radiation;
   b) providing one or more units configured to detect electromagnetic radiation;
   c) providing the one or more units within the defined volume;
   d) causing the one or more units to generate electromagnetic radiation at a first frequency;
   e) measuring the returned electromagnetic radiation using one or more of the units; and
   f) determining the location, identity, or level of one or more materials or the location of an interface between two materials within the defined volume based on the measurement of the returned electromagnetic radiation.

The apparatus and methods as described herein allow for a more accurate, more versatile and safer method than known previously. The apparatus and methods can also allow for the determination of the identity of the material surrounding each unit and it is possible to enable a profile of the defined volume to be established from which the position of any phase boundaries and, if desired, the thickness of any interphase regions, e.g. of foams or dispersions or emulsions, can be determined. The one or more units configured to generate/detect electromagnetic radiation are provided within the defined volume such that they are at least partially submerged within one or more material layers that may be present within the defined volume. Reference to "unit" or "units" in the specification refers to the unit or units configured to generate and/or detect electromagnetic radiation. The units may be electronic units. The units may be electromagnetic radiation generators. The units may be electromagnetic radiation detectors. The units may be antennae. Where the units are antennae, the antennae may emit electromagnetic radiation. The units may be resonators. The units may be transmission devices, such as bandpass filters. Where the units are resonators or transmission devices, they may generate a field of electromagnetic radiation. In this way, the material surrounding such units perturbs the resonances of the units in a characteristic way such that a determination of the material surrounding the unit can be made. The units may be non-nucleonic. The returned electromagnetic radiation which is detected will provide a signal which is characteristic of the material in which the units are located.

The method may comprise positioning the one or more units within any liquids present within the defined volume. The method may comprise providing one or more liquid materials within the defined volume and positioning the one or more units within the liquids.

In addition, the present invention does not rely on ionising radiation or radioactive sources and therefore avoids the regulatory requirements and environmental concerns associated with radioactive materials. As such, the present invention is non-nuclear or non-radioactive.

It will be appreciated that the apparatus and method will be used when there are one or more material phases within the defined volume such that the one or more units may be at least partially submerged within any such materials. For example, the method may be applied to an oil-water separator which will contain a mixture of oil, water and other components, such as gas and heavy hydrocarbons including tars. Having the units at least partially submerged within the material phases within the defined volume, which may be for example a separator vessel, allows the use of lower power, whereas previous methods rely on sources external to the material which is being measured, which requires much higher power levels. The submerged units may be closer to any interfaces between different materials and so a more accurate determination of the location of the interfaces may be provided. In addition, it is possible to determine the location of multiple interfaces which may be present between different materials. As such, the method of the present invention allows smaller units to be used and operates at a lower power whilst improving accuracy. This also allows the presence of an increased number of units within a given volume, which leads to more accurate measurement of the nature of the material in which the units are located. It is possible to determine the location of an interface between two material layers by comparing the measurements of units. In addition, since the units are submerged within the material within the defined volume, it is possible to use the system to analyse the nature of the material, whether the material is polar or non-polar, and it is not necessary to add any extra materials to the system for the method to function. The one or more units that are provided to generate electromagnetic radiation may be the same as or different to the one or more units provided to detect electromagnetic radiation. The identity of the material in which a unit is located may be determined by comparing the measured returned electromagnetic radiation to a known characteristic value or signal. The characteristic value or signal may be predetermined by submerging the unit in a known material, such as oil or water or a foam or emulsion, and measuring the signal returned to the unit. This can be done at different frequencies and/or temperatures for each material to provide a 'fingerprint' of the different materials within which the unit may be disposed. In the context of an oil-water separator, it has been found that there are identifiable differences between the signals received when a unit is submerged in oil or water and so it is possible to identify the location of each layer by means of these observed differences in signal. As such, even without comparing the returned signal to known values, it is possible to identify that different units are located within different material layers. Without wishing to be bound by scientific theory, it is believed that the near and/or far field interactions of the generated electromagnetic radiation with the material surrounding the units configured to generate and/or detect electromagnetic radiation alter the electromagnetic radiation in a way which is characteristic of the material with which the electromagnetic radiation interacts. As such, it is possible to determine the nature of the material in which the unit or units are disposed.

Certain prior art systems which use microwaves to detect the level of materials within a vessel locate the microwave source and detected outside of the vessel, meaning that larger and more highly powered sources are required. This limits the number of sources which can be provided and reduces the accuracy of the method and uses a greater amount of power or radioactive materials, which may have safety implications. Certain prior art systems are also not able to accurately measure the level of materials which are substantially transparent to microwave radiation, whereas the present invention allows for the measurement of the location or level of materials which do not absorb electromagnetic radiation at the chosen wavelength/frequency. This is because the unit(s) in the present invention are at least partially surrounded by material and so the signal detected by the unit(s) is characteristic of the material. Thus, by comparing the detected signal from one unit to either a signal which is known to represent one material or by comparing the signals detected by different units, it is possible to determine the nature and/or location of the material in which the unit is located.

One or more of the units may be configured to generate radiation at different frequencies and the method may further comprise altering the frequency of the radiation generated by one or more of the units. As such, it is possible to control the units to selectively generate radiation at desired wavelengths/frequencies, rather than only generating one wavelength/frequency. Of course, it will be appreciated that the units may only generate at a single wavelength/frequency if desired. Different units may be configured or caused to generate electromagnetic radiation at different frequencies. By altering the frequency/wavelength of the electromagnetic radiation used in the present method, it is possible to obtain additional data regarding the environment within which the units are located and thereby provide a more accurate picture of the material phases within the defined volume. For example, different frequencies may provide clearer characteristic signals depending on the material environment in which the units are located. In prior art systems which rely on radioactive materials, it is not possible to alter the energy of the radiation being released as this is characteristic of the radiation source provided and so there is no way in which different energies can be used to provide further information regarding the materials being measured.

The frequencies may be altered continuously or discontinuously. By continuously, it is understood that the units will generate electromagnetic radiation at a first frequency and then change to a different frequency by passing through the intermediate frequencies. By discontinuously, it is understood that the unit starts generating electromagnetic radiation at a first frequency and then switches to a different frequency without necessarily emitting the intermediate frequencies, obviously subject to the physical limitations of the unit. As such, continuous change would provide a more gradual change in frequency and discontinuous change would provide a stepped change in frequency. The electromagnetic radiation may be emitted continuously or may be pulsed. Similarly, the electromagnetic radiation may be detected continuously or in response to a pulsed emission.

The frequency of the electromagnetic radiation may be any suitable frequency, but is preferably microwave radiation or near-microwave radiation. The frequency of the electromagnetic radiation may be from about 0.5 GHz to about 200 GHz. The frequency of the electromagnetic radiation may be from about 1 GHz to about 10 GHz. The frequency may be from about 2 GHz to about 6 GHz. The frequency may be about 2.4 GHz. Any suitable frequency may be used and the frequency selected will may be determined on a case-by-case basis depending on which frequency provides optimal results. It is envisaged that the present method has particular, but not exclusive, application to the measurement of oil, water and/or solids such as sand, in an oil/water separator as well as any foam or emulsion layers. Microwave radiation has a sufficiently characteristic interaction with oil and water, even at low power, to allow a clear determination of the difference in returned signal. This is because microwave radiation is strongly absorbed by water, whereas it is only weakly absorbed by oil.

The one or more units may be connected to one or more signal generators and the signal generator(s) may be controlled to alter the signal provided to the one or more units to cause the one or more units to generate electromagnetic radiation at a predetermined frequency. Preferably a single signal generator is used, but it will be appreciated than any number of signal generators may be used as required. The signal generator may control the frequency at which the units generate electromagnetic radiation and thereby allow the units to generate different frequencies as required. The signal generator(s) may comprise any suitable control means.

The method may further comprise causing one unit to generate electromagnetic radiation and detecting any returned electromagnetic radiation. In other words, the same unit may be used as both the generator and receiver/detector of the electromagnetic radiation. As such, a signal, preferably in the microwave frequency band, may be sent from a signal generator down a feed line, which may be a coaxial cable, to the unit to cause the unit to generate electromagnetic radiation at the chosen frequency. Electromagnetic radiation may interact with the material surrounding the antenna and some may be returned, whether by reflection or other mechanisms, and back down the feed line. The ratio of the transmitted signal to the returned signal is referred to as the standing wave ratio. The standing wave ratio is dependent on the electrical properties of the materials surrounding the antenna as well as the geometrical properties of the antenna itself. As the geometrical properties of the antenna are known and fixed, the standing wave ratio is therefore characteristic of the material surrounding the unit. In this way, it is possible to determine the environment in which the unit is located and to detect when this changes. The perturbation of resonances by a surrounding material may also be used to determine the nature of the material in question.

The method preferably includes providing a plurality or an array of units, namely two or more. Where there is a plurality or array of units, it is possible to determine the environment of the units and thereby determine the location of one or more interfaces by comparing the signal received by the units. Where the method is used in respect of a water/oil separator, the water has a much higher permittivity and conductivity than oil, so the change in signal when the electromagnetic radiation has interacted with water or oil is marked and the location of an interface between the oil and water may be determined by simply comparing the signals of the units. In some cases, there may not be a clearly delineated interface between the two materials. For example, in a water/oil separator, there may be an emulsion layer which provides a different signal compared to a water layer or an oil layer. The method of the present invention allows the identification of the presence of such layers. Similarly, there may be a foam layer or other interphase layer present. Again, the method of the present invention is able to determine the presence and location of such a layer due to the difference in signal provided by the unit or units located within the foam layer or other interphase layer when compared to the signal provide by units disposed in the water layer or in the oil layer, or indeed any other layer.

Alternatively, or additionally, the method may comprise causing one unit to generate electromagnetic radiation and detecting any returned electromagnetic radiation with one or more other units. In this way, the electromagnetic radiation may be generated by one unit and then received by one or more other units. The electrical properties of the material between the units attenuates or otherwise alters the electromagnetic radiation in a characteristic manner. Again, the signal variation is environment and geometry dependent. As such, since the geometry is fixed and the frequency can be adjusted as required, the signal generated is characteristic of the material between the units. The signal can be compared to known signals which correspond to different environments or materials, such as oil, water, sand, emulsion, or foam or other interphase layers, and the location of such material layers within a vessel can be determined or simply determined from a comparison of the signals provided by the units.

As such, the method may further comprise calculating the standing wave ratio and/or the attenuation or other change of the electromagnetic radiation on the basis of the generated and detected electromagnetic radiation and identifying the material surrounding the unit or units based on the calculated standing wave ratio and/or the attenuation or other change respectively. Calculating can be understood to mean measuring or determining. Other changes may also include shifts in frequency. The absolute values of the standing wave ratio or attenuation or any other parameter measured may not be necessary to measure, although this may be done, and it is the relative values between different units and/or the values relative to known environments which may be used in determining the profile of the materials within the defined volume.

Preferably, the method includes providing a plurality or array of units. Any suitable number of units may be provided. Preferably, at least two units are provided. Preferably, each unit is configured or operated to generate and/or detect electromagnetic radiation. By providing a plurality of units, it is possible to determine the location of layers of different materials within a defined volume, such as a vessel like a separator. Unlike prior art systems which comprise a single electromagnetic radiation source, providing an array of units, namely two or more units, results in a more precise determination of the materials in a vessel, particularly the location of such materials.

In addition, with two or more units, the units can be operated in a number of ways to more accurately determine the location of different materials within a given volume. It also allows the location of more than one interface between materials to be determined, whereas prior art systems are only configured to determine the location of one interface.

The method may include sequentially causing one of the units to generate electromagnetic radiation at the first frequency, detecting any returned radiation with either the same unit or one or more of the other units, identifying the material surrounding the unit based on the detected electromagnetic radiation, and determining the level of one or more material phases or the location of an interface between two material phases within the defined volume based on the returned radiation. It will be appreciated that the units can be activated in any sequence, although it is contemplated that the units will be activated in consecutive order. The material surrounding the units may be identified by comparing the calculated standing wave ratio and/or the measured attenuation to known values or simply based on a comparison between the signals received from different units. The method may also operate on the basis of one unit generating the electromagnetic radiation and all of the units in the array detect any returned electromagnetic radiation.

It will be appreciated that the method may be applied to a dynamic system in which the level of one or materials changes over time and so the method may be repeated as often as required. The method may be repeated at one or more frequencies which are different to the first frequency. Any suitable frequency may be used as long as it interacts with the different materials within a defined volume and provides a different return signal depending on the material in which the unit is located. The method may be repeated one or more times at each frequency and the method is not particularly limited by the number of times it is repeated. The frequency at which the method is repeated will depend on the operating requirements. For example, it may be repeated continuously with little or no downtime between cycles or it may be repeated at predetermined intervals depending on whether frequent sampling is required.

An apparatus is provided for determining the identity, location or level of one or more material phases or the location of an interface between two material phases within a defined volume, the apparatus comprising: an array of units configured to generate and detect electromagnetic radiation, and an enclosure containing the array of units, the apparatus being configured to be at least partially submerged within one or more material phases within the defined volume.

The array of units is located within the defined volume such that, when there is material within the defined volume, the array is at least partially submerged in the material. This allows the nature of the material in which the units are disposed to be determined and by combining the date from each unit, it is possible to build up a picture of the distribution of material phases within a defined volume. The array of units is preferably disposed entirely within the enclosure. The enclosure may fully or partially contain the array of units. Preferably the enclosure fully contains the array of units to protect the units from the materials to which the apparatus is exposed.

The apparatus may be substantially linear. The apparatus may be substantially elongate. Since it is intended to determine the distribution of material phases within a defined volume, it is preferable to have the apparatus extend substantially the entire height of the defined volume so that a profile of the defined volume can be determined. This configuration optimises vertical resolution and compactness of the apparatus. The limit of the vertical resolution is determined by the size of the units configured to generate and/or detect electromagnetic radiation and since the present invention allows for the use of units which are smaller than those of the prior art, a greater number can be used which increases the resolution of the apparatus.

The apparatus may further comprise one or more support members which retain the units within the enclosure. As previously indicated, the units may comprise antennae and/or resonators. Preferably, the support members comprise means for retaining the units in a desired orientation. The support members may also be adapted to connect to one or more other support members. The invention is not particularly limited to the exact way in which the support members may be connected to one another and may include any suitable connection means. As such, the support members can form a modular system. As such, the number of units configured to generate and/or detect electromagnetic radiation in an array can be adjusted depending on the size of the vessel in which the apparatus is to be used. Each support member may support any number of units as required. For example, the support members may be configured to support one, two, three, or more units. As such, the present invention provides greater flexibility with regards to the size of the apparatus and can be readily configured for different sizes of vessel by selecting the number of modular units to include in the apparatus. Since vessels may come in many different sizes, it is desirable to provide an apparatus which is the optimal size for each vessel. In addition, in the event that a unit configured to generate and/or detect electromagnetic radiation becomes defective, it is possible to quickly and easily replace any defective antennae by swapping out the module comprising the defective part. The enclosure may or may not be modular. Where the enclosure is modular, it may be configured to allow the modules to be connected to one another. Again, the invention is not particularly limited by the exact means of connection, but may include, for example, a push-fit type connection, an interference connection or a threaded connection.

The enclosure is preferably at least partially transparent to the electromagnetic radiation generated by the units configured to generate and/or detect electromagnetic radiation. Since the present invention relies on the differing interactions between the electromagnetic radiation generated by the units and the materials with which the electromagnetic radiation interacts, it is necessary for the radiation to interact with the material surrounding the apparatus. As such, the enclosure containing the units must allow at least a portion of the radiation to interact with the surrounding material.

The enclosure may be made of any suitable material, including ceramic, plastic or metal. By suitable, it is understood that the material must be able to withstand the conditions within the defined volume. For example, where the apparatus is provided in an oil-water separator, the enclosure must be able to be disposed in water and oil without damage.

The enclosure may comprise one or more windows which are more transparent to electromagnetic radiation than the rest of the enclosure. So that the electromagnetic radiation may readily interact with the material surrounding the apparatus, the units may be arranged to provide the radiation through one or more windows. The windows are preferably made of a material which is relatively more transparent to the given wavelength of radiation than the enclosure. The windows may be removable to allow access to the units configured to generate and/or detect electromagnetic radiation.

The enclosure may be in any suitable form, but is preferably in the form of a pipe. The pipe may have any cross-section and the invention is not particularly limited to any specific cross-section, but the pipe may have a substantially circular cross section.

Each unit in the array may be connectable to a signal generator. It is not necessary for each unit to be connected to a signal generator simultaneously and the apparatus may comprise a switching means to selectively connect the units in the array to one or more signal generators. This will depend on how the units are operated to provide the characteristic signal.

The units may be antennae. The antennae may comprise any suitable antennae. The antennae may be patch antennae. The antennae may be omnidirectional or directional antennae or a combination of the two.

The units may be resonators or transmission devices. The resonators may be any suitable resonators.

The units may be any suitable power. Preferably, the units each have a power in the range of from about 1 pW (picowatt) to about 7 W. The units may have powers in the nanowatt range.

The units may have powers in the microwatt range. The relatively low power means that the apparatus is cheap to operate and has low safety risk.

The apparatus may comprise one or more temperature sensors. The temperature sensors can be any suitable type of temperature sensor and the invention is not particularly limited by the type of sensor used.

The apparatus may be a level gauge.

The apparatus may comprise data processing means capable of receiving a signal from each unit and determining therefrom a characteristic of the fluid material at the location of the unit from which the signal is received. As already described, the signal detected by a unit is characteristic of the material surrounding the unit and so it is possible to determine the nature of the fluid material from processing the signal received from each unit.

The apparatus may be provided in combination with an oil-water separator vessel, the apparatus being preferably disposed substantially vertically in the vessel. Since the apparatus of the present invention has particular application to determining the levels of water and oil within a separator, the apparatus is preferably provided within an oil-water separator vessel.

The separator vessel may have at least one fluid inlet means for permitting the inflow of a mixture of oil, gas and water, and at least one fluid outlet for permitting the flow of oil, gas and water from the vessel. The apparatus according to the second aspect of the present invention is preferably positioned at least partially within the vessel.

There is also provided a method of measuring the profile of a multi-phase medium comprising positioning the apparatus according to the second aspect of the present invention such that at least a part of the said array of units configured to generate and/or detect electromagnetic radiation is positioned in a region of the medium in which different phases are at least partially separated.

The method of any aspect of the present invention may comprise the step of using the apparatus described herein as part of a control feedback loop for controlling an oil-water separator containing a multi-phase medium.

The method of any aspect of the present invention may be characterised in that the position of the phase boundaries/interfaces is determined by analysing the electromagnetic radiation detected by the one or more units and an inlet flow rate to and/or one or more outlet flowrates from the defined volume, for example an oil-water separator vessel, are controlled to maintain the position of the interface within predetermined limits. Since it is possible to determine the location of interfaces between materials within a vessel using the method and apparatus of the present invention, this information may be used to control the rate at which material, such as a mixture of oil and water, is provided to a vessel, and/or to control the rate at which oil and water which have been separated from one another are withdrawn and thereby control the level of the interface between the oil and water within the vessel. In addition, the method and apparatus of the present invention is able to detect the existence of foams or interphase layers and provide some feedback so that any suitable adjustments can be made to the system. As such, the thickness of any interphase layers, including layers which comprise mixtures of two materials, or foam layers may be determined by the methods and apparatus of the present invention and the concentration of chemicals added to the defined volume to reduce the formation of such interphase layers or foam layers is controlled to maintain the thickness of the interphase or foam layers within predetermined limits.

In any aspect of the present invention, the material may be a liquid or a gas.

It will be appreciated that any features described in connection with one aspect of the present application may equally be applied to any other aspect of the present application, and all such combinations are explicitly considered and disclosed herein. As such, the apparatus of the of the present invention is adapted to provide any of the method steps described herein, and vice versa.

BRIEF DESCRIPTION OF THE DRAWINGS

The invention will be further described by way of example only with reference to the following figures, of which.

DETAILED DESCRIPTION

Whilst the present invention is described with regards to an oil-water separator, it will be appreciated that the methods and apparatus of the present invention may be used for any vessel in which the level of one or more materials is desired to be known.

Figure 1:
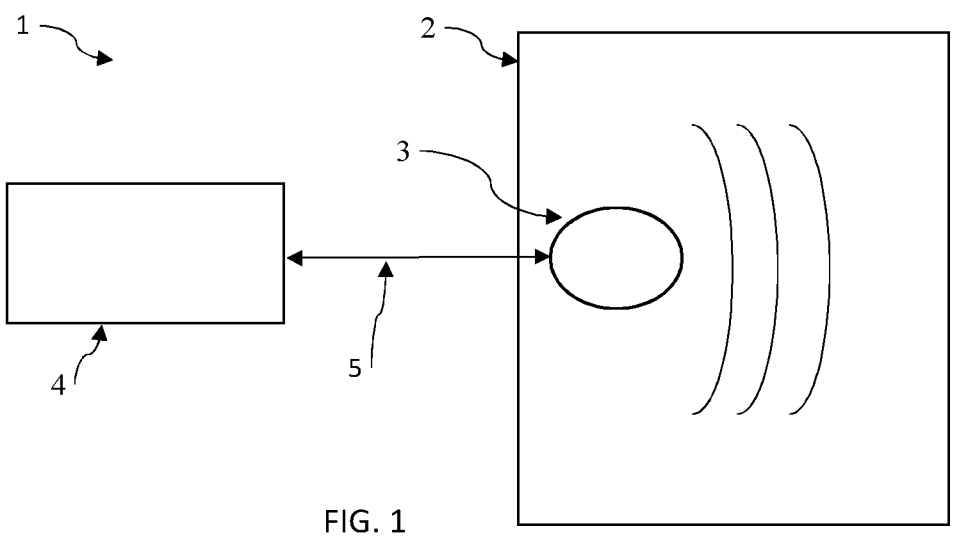
FIG. 1 is a schematic depiction of a configuration in which a unit generates and receives electromagnetic radiation.

FIG. 1 is a schematic depiction of one way in which the method and apparatus of the invention may function, relying on a measurement of the standing wave ratio. The apparatus 1 is generally depicted as comprising a vessel 2, which in the exemplary depictions is an oil-water separator. A unit 3 configured to generate and detect electromagnetic radiation is schematically depicted and is located within the vessel 2. The unit 3 is connected to controller 4 which comprises the electronics used to control the unit 3 and to receive the signal returned by unit 3. The unit 3 is connected to the controller 4 by a coaxial cable 5, but the invention is not limited to co-axial cables. In this configuration, the controller 4 causes the unit 3 to generate electromagnetic radiation, generally depicted by the three curved lines, which interacts with the material surrounding the unit 3. At least some of the generated electromagnetic radiation is returned to the unit 3 through reflection or any other means and passed back down the cable 5 to the controller 4 where the returned signal is processed and the identity of the material in which the unit 3 is located is determined. The returned spectrum is characteristic of the material in which the unit 3 is disposed. This may be affected by near or far field interactions of the electromagnetic radiation and the surrounding material. The controller 4 may vary the frequency of the signal to cause the unit 3 to generate different frequencies of electromagnetic radiation in order to provide more information regarding the environment of the unit 3. The radiation may be emitted from the unit 3 and interact with the material before returning to the unit 3. The radiation may not be emitted from the unit 3 but perturbed by the material surrounding the unit 3.

Figure 2:
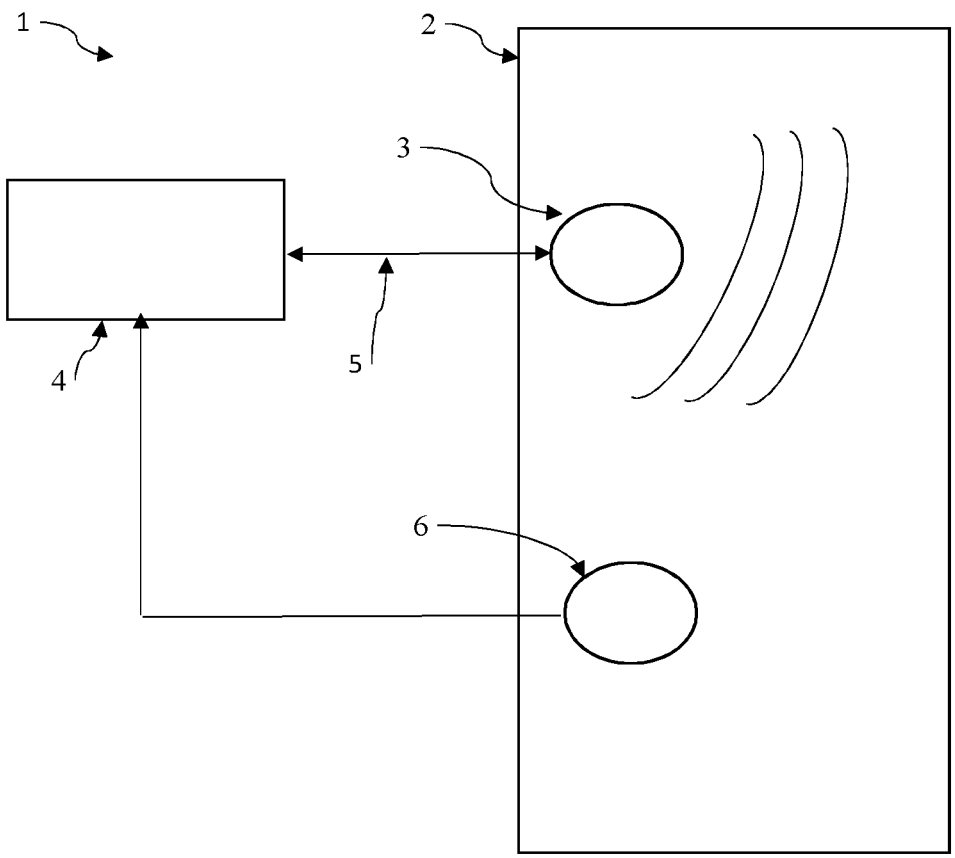
FIG. 2 is a schematic depiction of a configuration in which a unit generates electromagnetic radiation which is detected by another unit.

FIG. 2 depicts a similar setup to FIG. 1, but additionally depicts a second unit 6. In this additional or alternative method of operation of the present invention, the first unit is caused to generate electromagnetic radiation into the surrounding material and the electromagnetic radiation is detected by the second unit 6 which passes the signal back to the controller 4 for determination of the material with which the electromagnetic radiation has interacted. The signal detected by the second unit 6 is not only representative of radiation passing from the first unit 3 to the second unit 6 by line of sight, but has surprisingly been found to be characteristic of the material around the units 3, 6. As such, the second unit 6 will detect a spectrum of electromagnetic radiation which can be characterised to determine the material surrounding the units 3,6. One or both of the techniques depicted in FIG. 1 or 2 can be selected to provide the optimal noise-to-signal ratio depending on the circumstances.

Figure 3:
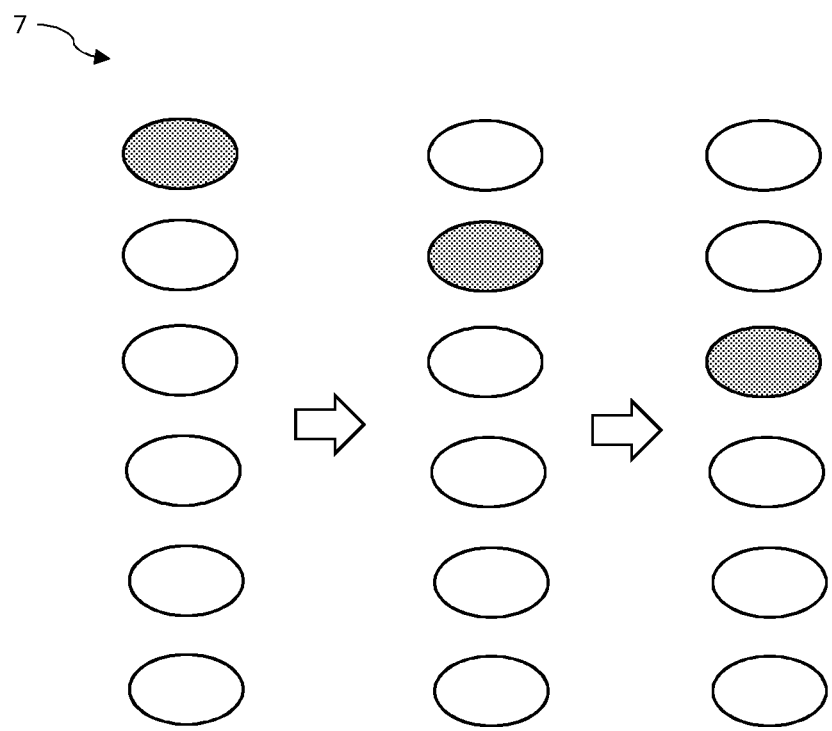
FIG. 3 is a schematic depiction of a configuration in which a single unit in an array generates and detects electromagnetic radiation and the units are polled sequentially.

FIG. 3 is a schematic depiction of an array 7 of units, which may be antennae. Only a section of the array is depicted, and the array may comprise any number of units as required. This figure depicts the operation in which units in the array 7 are sequentially operated to generate and detect electromagnetic radiation. As depicted, in a first operation, the topmost unit generates and detects electromagnetic radiation and the nature of the material surrounding the unit may therefore be determined. In a second operation, the second to top unit is operated as described herein and the nature of the material surrounding that unit may therefore be determined. This continues with the remaining units. As depicted, the units are operated starting from the uppermost and consecutively down towards the lowermost unit. It will be appreciated that the units need not necessarily be operated in consecutive order and any sequence may be selected. Also, the selection of the first unit to operate is arbitrary, although it is likely that the unit at one end of the apparatus or the other will be operated first.

Figure 4:
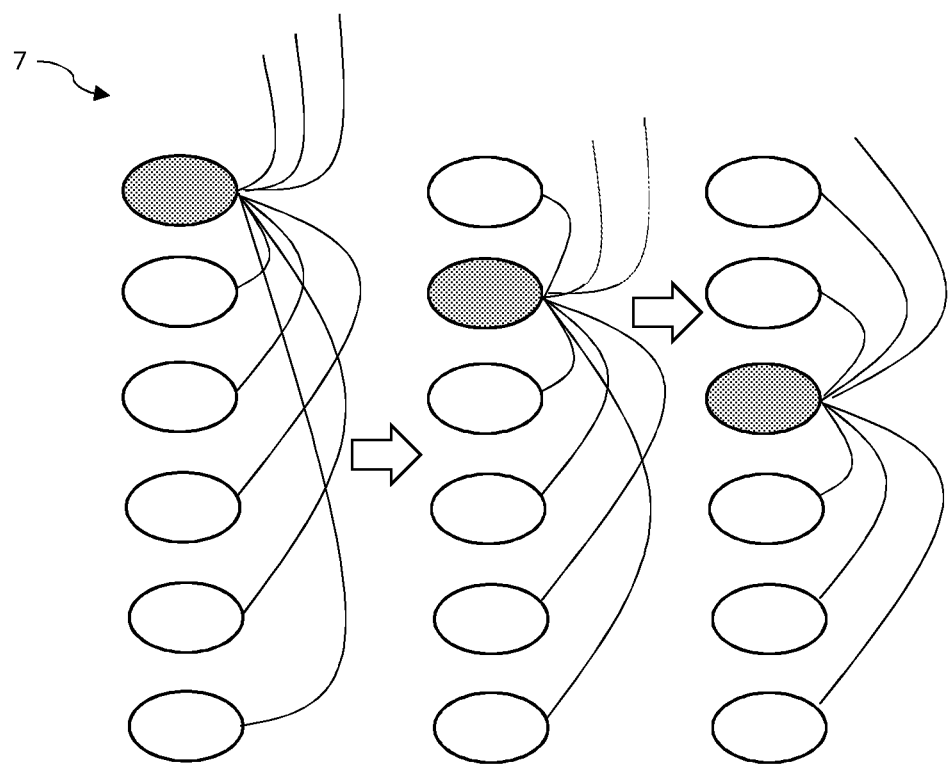
FIG. 4 is a schematic depiction of a configuration in which a single unit in an array generates electromagnetic radiation and the other units in the array detect the electromagnetic radiation.

FIG. 4 is a further schematic depiction of another way in which an array of units configured to generate and/or detect electromagnetic radiation may be operated. Only a section of the array is depicted and the array may comprise any number of units as required. The mode of operation is similar to that depicted in FIG. 3, but one of the units is operated to generate electromagnetic radiation and the other units are operated to detect any returned electromagnetic radiation. The lines connecting the various units are simply to demonstrate that the electromagnetic radiation may pass from one of the units to the others and is not intended to be an accurate depiction of the actual path of the electromagnetic radiation. Again, as with the mode of operation depicted in FIG. 3, the units are polled sequentially and the detected electromagnetic radiation signal is used to determine the level of one or more materials within the vessel in which the units are disposed. It will be appreciated that the different modes of operation depicted in FIGS. 3 and 4 can be selected depending on the requirements of the system and may be complementary to one another. As such, the method can employ one or both modes of operation.

Figure 5A:
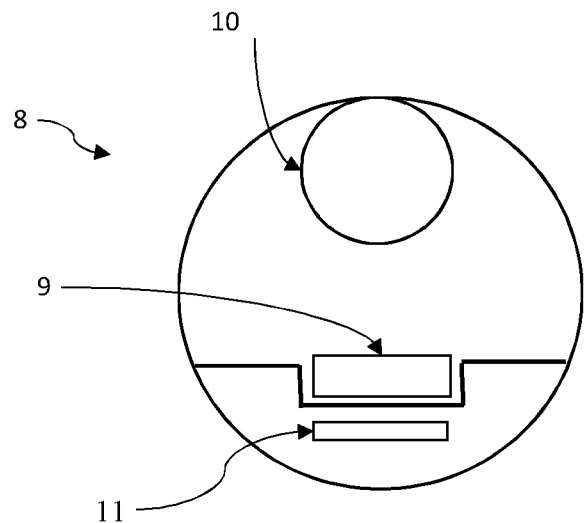
FIGS. 5a and 5b are schematic depictions of an exemplary support member.

FIG. 5*a* is an end-on schematic depiction of a support member 8. This is an exemplary support member module 8 and depicts one possible embodiment. The support member 8 is substantially circular and has an outer diameter which allows it to be inserted into a pipe. The cross-sectional shape of the support member 8 may be selected to generally match the cross-sectional shape of the enclosure into which the support member 8 is inserted. Other cross-sectional shapes are contemplated, including, but not limited, to square, oval, and triangular. The unit configured to generate and/or detect electromagnetic radiation 9 is located within the outer circumference of the support member 8 and may be attached to the support member 8 by any suitable means. For example, the unit 9 may be attached to the support member 8 by an adhesive. Additionally, or alternatively, the unit 9 may be retained by one or more clips or receiving portions. The support member 8 may optionally also include a locating means 10 which is configured to receive a supporting rod (not shown). Where there is a plurality of support members 8 joined together, a supporting rod may be inserted through the locating means 10 to add rigidity to the resulting structure. Again, it will be appreciated that any suitable shape of locating means 10 may be used. The support member 8 comprises a flattened portion onto which the unit 9 may be attached. In the depicted embodiment, the support member 8 also comprises a protrusion 11 which extends from the support member 8 and is configured to engage with a corresponding recess in an adjacent support member 8. In this way, the support members 8 can be joined together as part of a modular system. It will be appreciated that any connecting means can be used to join support members together and the connecting means may take any form.

Figure 5B:
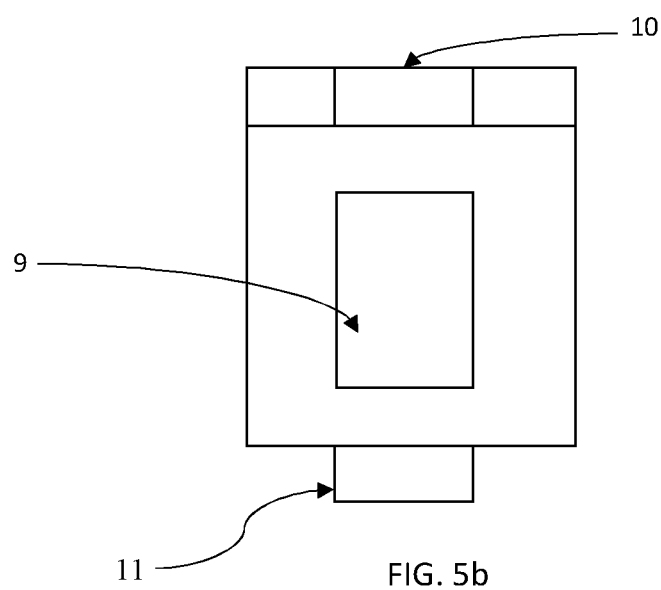

FIG. 5*b* depicts in plan view a support member 8 according to the present invention. Although from this perspective, it may not be possible to see the locating means 10, the two vertical lines inward to the outer lines depict the location of the locating means 10 to aid understanding. The locating means may extend the entire length of the support member 8, but in this embodiment are depicted as only extending a portion of the length of the support member 8. The unit 9 is depicted as a rectangular shape, but this is schematic and the shape of the unit 9 is not particularly limited. Protrusion 11 is depicted as extending from the support member and the corresponding receiving means at the opposite end of the support member 8 is not shown. Since the present invention does not use ionising radiation, it is possible to make the support member from lightweight materials such as plastic. In addition, it is also possible to 3D print the support members 8. The support member 8 is configured to have a void space through which electrical connections can pass.

Figure 6:
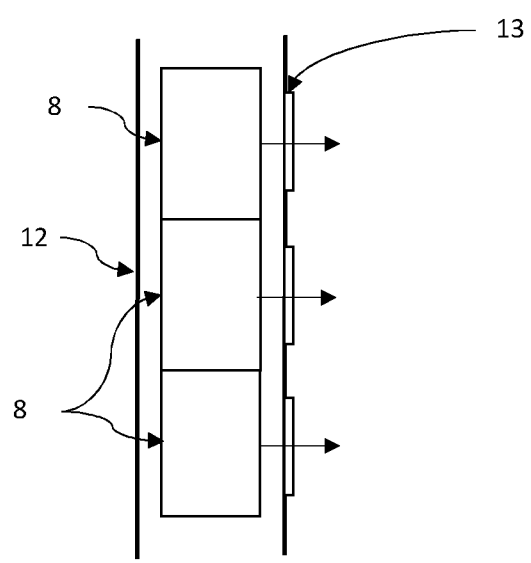
FIG. 6 is a schematic depiction of a cross-section through an apparatus.

FIG. 6 depicts a schematic cross-sectional view of a plurality of support members 8 within an enclosure 12. Only a section of the apparatus is depicted and there may be more than three support members 8 present. In addition, a gap is shown between the enclosure 12 and the outer portions of the support members 8. Whilst there may be a gap, preferably, the outer face of the support members 8 is at least partially in contact with the inner face of the enclosure 12 to retain the support members 8 and thereby the units 9 in the correct location. Also depicted are windows 13 which are located to allow electromagnetic radiation to pass out of and back into the enclosure 12. In some embodiments, there may be no windows present with the electromagnetic radiation passing through the wall of the enclosure 12. When used in fluid environments the enclosure 12 may be a dip tube that provides mechanical (against pressure) and chemical resistant barrier between the electronics and the materials being profiled. The material is chosen to have sufficient strength and chemical resistance.

Figure 7:
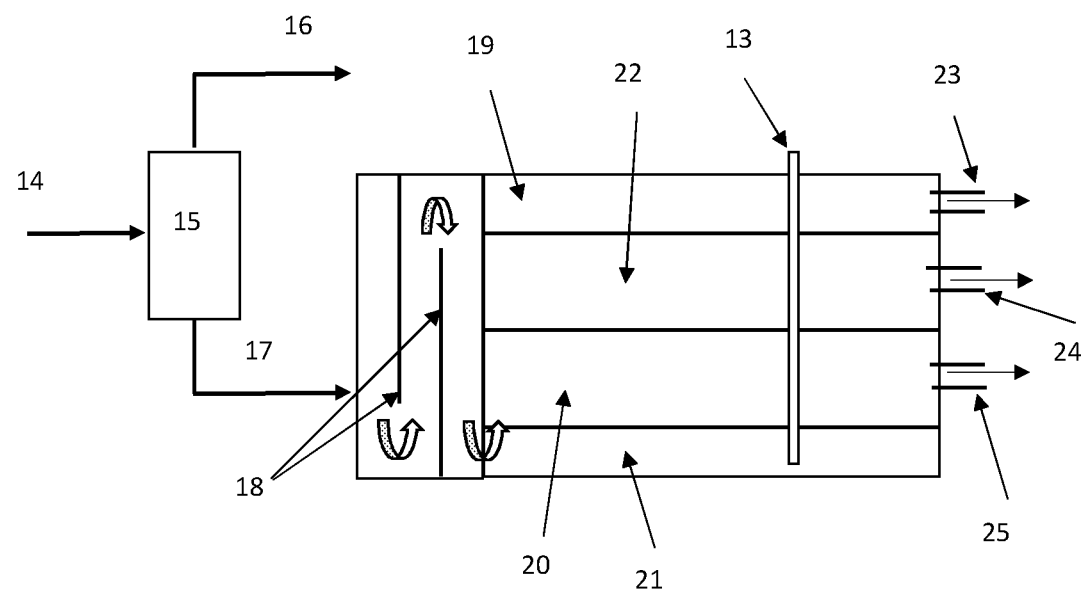
FIG. 7 is a schematic depiction of an oil-water separator including the apparatus.

FIG. 7 is a schematic depiction of the apparatus according to the present invention located within an oil-water separator. The enclosure 13 is shown as arranged in a vertical array that extends substantially the whole height of the separator. The enclosure 13 passes through a wall of the separator vessel and is immersed in the material layers within the vessel. The input flow 14 is a mixture of oil, gas, and water which is passed into a pre-treated 15 to effect preliminary separation of gas which is taken off via line 16, usually for further processing. Liquids, namely oil and water are taken off via line 17. The fluid flow is slowed and rendered less turbulent by baffles 18 before separating into layers of gas 19, water 20, oil 22, and sand or sediment 21. The separate layers flow out of the vessel through respective ports 23, 24, 25. A further port (not shown) may be provided to remove sand or sediment 21. In operation, the signal detected by each of the units in the array within the enclosure 13 is processed to determine the nature of the material within which each unit is located and thus the locations and depths of each of the layers can be determined throughout the separator. It is also possible to determine the presence, location and thickness of any undesirable mixed layers between the gas and water, and between the water and oil layers.

In summary, the present invention provides for a safer, more compact and more accurate method and apparatus for determining the profile of materials within a defined volume, such as an oil-water separator. The method and apparatus allow for the identification and location of boundaries between different materials, and is also eminently suitable for identifying the presence of mixed layers, such as foams or emulsions. The present invention does not rely on radioactive sources so handling of the apparatus is easier and safety precautions associated with radioactive materials can be avoided. It is also possible to use a range of frequencies and energies to obtain information about the environment in which the units configured to generate and/or detect electromagnetic radiation are located. Furthermore, the apparatus is able to use low power and low voltages which further improves safety. There are no moving parts in the apparatus and the apparatus is controlled electronically so that there is reduced scope for failure. In addition, since the apparatus may be modular, any defective components can be readily replaced and maintenance is also made easier. The method and apparatus of the present invention is also more resistant to build up of contaminants on the surface of the apparatus since the level of the materials may be determined by comparing the signals received by the units used rather than absolute values, although absolute values may also be used.

Certain features of the method and apparatus as described herein are set out in the following clauses.

1. A method for determining a location, identity or level of one or more material phases or the location of an interface between two material phases within a defined volume, said method comprising:
    a) providing one or more units configured to generate electromagnetic radiation;
    b) providing one or more units configured to detect electromagnetic radiation;
    c) providing the one or more units within the defined volume;
    d) causing the one or more units to generate electromagnetic radiation at a first frequency;
    e) measuring the returned electromagnetic radiation using one or more of the units; and
    f) determining the location, identity or level of one or more materials or the location of an interface between two materials within the defined volume based on the measurement of the returned electromagnetic radiation.
2. The method according to Clause 1, wherein one or more of the units are configured to generate electromagnetic radiation at different frequencies, preferably in the range of from 0.5 GHz to 200 GHz, and the method further comprises altering the frequency of the radiation generated by one or more of the units.
3. The method according to Clause 1 or 2, wherein the one or more of the units are connected to one or more signal generators, preferably a single signal generator, and the method further comprises controlling the one or more signal generators to alter the signal provided to one or more units to cause the one or more units to generate electromagnetic radiation at a predetermined frequency.
4. The method according to any of Clauses 1 to 3, the method further comprising causing one unit to generate electromagnetic radiation and detecting any returned electromagnetic radiation with same unit and/or causing one unit to generate electromagnetic radiation and detecting any returned electromagnetic radiation with one or more other units.
5. The method according to Clause 4, the method further comprising calculating the standing wave ratio and/or the attenuation of the electromagnetic radiation on the basis of the emitted and detected electromagnetic radiation and identifying the material surrounding the unit or units based on the calculated standing wave ratio and/or the attenuation respectively.
6. The method according to any of Clauses 1 to 5, the method comprising:
    i) providing an array of units;
    ii) sequentially causing one of the units to generate electromagnetic radiation at the first frequency;
    iii) detecting any returned radiation with either the same unit or one or more of the other units;
    iii) identifying the material surrounding the unit based on the detected electromagnetic radiation; and
    iv) determining the level of one or more material phases or the location of an interface between two material phases within the defined volume based on the returned radiation
7. The method according to Clause 6, wherein the material surrounding the unit(s) is identified by comparing a calculated standing wave ratio and/or the measured attenuation to known values.
8. The method according to any preceding clause, wherein the method is repeated at one or more frequencies which are different to the first frequency.

9. An apparatus for determining the identity, location or level of one or more material phases or the location of an interface between two material phases within a defined volume, the apparatus comprising:
a) an array of units configured to generate and detect electromagnetic radiation;
b) an enclosure containing the array of units; the apparatus being configured to be at least partially submerged within one or more material phases within the defined volume.
10. The apparatus of Clause 9, wherein the apparatus is substantially linear.
11. The apparatus of Clause 9 or 10, wherein the apparatus further comprises one or more support members which retain the units within the enclosure, preferably wherein the support members are adapted to connect to one or more other support members.
12. The apparatus according to any of Clauses 9 to 11, wherein the enclosure is at least partially transparent to the electromagnetic radiation generated by the units.
13. The apparatus according to any of Clauses 9 to 12, wherein the enclosure is at least partially comprised of ceramic, plastic, or metal.
14. The apparatus according to any of Clauses 9 to 13, wherein the enclosure comprises one or more windows which are more transparent to electromagnetic radiation than the rest of the enclosure.
15. The apparatus according to any of Clauses 9 to 14, wherein each unit in the array is connectable to a signal generator.
16. The apparatus according to any of Clauses 9 to 15, wherein the apparatus comprises a switching means to selectively connect the units in the array to a or the signal generator.
17. The apparatus according to any of Clauses 9 to 16, wherein the units comprise antennae, preferably wherein the antennae comprise patch antennae.
18. The apparatus according to any of Clauses 9 to 17, wherein the units have a power in the range of from 1 pW (picowatt) to 7 W.
19. The apparatus according to any of Clauses 9 to 18 further comprising one or more temperature sensors.
20. The apparatus according to any of Clauses 9 to 19 wherein the apparatus is modular.
21. The apparatus according to any of Clauses 9 to 20 further comprising data processing means capable of receiving a signal from each unit and determining therefrom a characteristic of the fluid material at the location of the unit from which the signal is received.
22. The apparatus according to any of Clauses 9 to 21 provided in combination with an oil/water separator vessel, the apparatus preferably being disposed substantially vertically in the vessel.
23. The apparatus according to any of Clauses 9 to 22, wherein the apparatus is a level gauge.
24. A method of measuring the profile of a multi-phase medium comprising positioning the apparatus according to any of Clauses 9 to 23 such that at least part of said array of units is positioned in a region of the medium in which different phases are at least partially separated.
25. The method of any of Clauses 1 to 8 or 24 comprising the step of using the apparatus of any of Clauses 9 to 23 as part of a control feedback loop for controlling an oil-water separator containing a multi-phase medium.
26. The method of any of Clauses 1 to 8 or 24 or 25, wherein the position of interfaces between material layers is determined by analyzing the electromagnetic radiation detected by the one or more units and controlling an inlet flow rate to and/or one or more outlet flowrates from the defined volume to maintain the position of the interface within predetermined limits.
27. The use of an apparatus according to any of Clauses 9 to 23 to determine the location, identity or level of one or more materials or the location of an interface between two materials within a defined volume.

The invention claimed is:

1. An apparatus for determining the identity, location or level of one or more material phases or the location of an interface between two material phases within a defined volume, the apparatus comprising:
   a) a linear array of units configured to generate and detect electromagnetic radiation;
   b) an elongate enclosure containing the array of units, the elongate enclosure being at least partially transparent to the electromagnetic radiation generated by the units;
   the apparatus being configured to be at least partially submerged within the one or more material phases within the defined volume with the linear array of units being physically isolated from the one or more materials by the elongate enclosure,
   the linear array of units being configured to generate transmission signals through the at least partially transparent elongate enclosure to the one or more material phases surrounding the enclosure at locations along the length of the enclosure, and to receive return signals through the elongate enclosure at locations along the length of the enclosure from the one or more material phases surrounding the enclosure,
   wherein the apparatus is configured to process the return signals to determine the identity, location or level of the one or more material phases or the location of an interface between two material phases within the defined volume.

2. The apparatus according to claim 1, wherein the enclosure comprises one or more windows which are more transparent to electromagnetic radiation than the rest of the enclosure, the units being configured to transmit and receive electromagnetic radiation through the windows.

3. The apparatus according to claim 1, wherein each unit in the array is connectable to a signal generator.

4. The apparatus according to claim 3, wherein the apparatus comprises a switch to selectively connect the units in the array to the signal generator.

5. The apparatus according to claim 1, wherein the units comprise antennae.

6. The apparatus according to claim 1, wherein the units have a power in the range of from 1 pW to 7 W.

7. The apparatus according to claim 1, further comprising one or more temperature sensors.

8. The apparatus according to claim 1, further comprising a data processor capable of receiving a signal from each unit and determining therefrom a characteristic of the material surrounding the enclosure at the location of the unit from which the signal is received.

9. The apparatus according to claim 1 provided in combination with an oil/water separator vessel, the apparatus being disposed vertically in the vessel.

10. A method for determining a location, identity or level of one or more material phases or the location of an interface between two material phases within a defined volume, said method comprising:
    a) positioning the apparatus according to claim 1 within the material in the defined volume;
    b) causing the array of units to generate electromagnetic radiation;

c) measuring the returned electromagnetic radiation using the array of units; and d) determining the location, identity or level of one or more materials or the location of an interface between two materials within the defined volume based on the measurement of the returned electromagnetic radiation.

11. The method according to claim 10, wherein one or more of the units are configured to generate electromagnetic radiation at different frequencies, and the method further comprises altering the frequency of the radiation generated by one or more of the units.

12. The method according to claim 10, wherein the units are connected to one or more signal generators, and the method further comprises controlling the one or more signal generators to alter the signal provided to the units to cause the units to generate electromagnetic radiation at a predetermined frequency.

13. The method according to claim 10, the method further comprising causing one unit to generate electromagnetic radiation and detecting any returned electromagnetic radiation with same unit and/or causing one unit to generate electromagnetic radiation and detecting any returned electromagnetic radiation with one or more other units.

14. The method according to claim 13, the method further comprising calculating a standing wave ratio and/or an attenuation of the electromagnetic radiation on the basis of the emitted and detected electromagnetic radiation and identifying the material surrounding the unit or units based on the calculated standing wave ratio and/or the attenuation respectively.

15. The method according to claim 10, the method comprising:

i) sequentially causing one of the units to generate electromagnetic radiation at a first frequency;

ii) detecting any returned radiation with either the same unit or one or more of the other units;

iii) identifying the material surrounding the unit based on the detected electromagnetic radiation; and iv) determining the level of one or more material phases or the location of an interface between two material phases within the defined volume based on the returned radiation.

* * * * *